(12) United States Patent
Shalev et al.

(10) Patent No.: US 8,420,112 B2
(45) Date of Patent: Apr. 16, 2013

(54) SOLID DOSAGE FORM FOR TREATING HEADACHES

(75) Inventors: Alon Shalev, Raanana (IL); Itschak Lamnsdorf, Modi'in (IL)

(73) Assignee: Paindure Ltd., Herzliya Pitvach (IL)

( * ) Notice: Subject to any disclaimer, the term of this patent is extended or adjusted under 35 U.S.C. 154(b) by 27 days.

(21) Appl. No.: 12/922,719

(22) PCT Filed: Mar. 19, 2009

(86) PCT No.: PCT/IL2009/000314
§ 371 (c)(1),
(2), (4) Date: Sep. 15, 2010

(87) PCT Pub. No.: WO2009/116047
PCT Pub. Date: Sep. 24, 2009

(65) Prior Publication Data
US 2011/0008408 A1    Jan. 13, 2011

Related U.S. Application Data

(60) Provisional application No. 61/038,431, filed on Mar. 21, 2008.

(51) Int. Cl.
*A61M 31/00* (2006.01)
*A61K 31/167* (2006.01)
*A61P 25/06* (2006.01)
*A61P 25/08* (2006.01)

(52) U.S. Cl.
USPC ............................ 424/425; 424/424; 514/626

(58) Field of Classification Search .................... None
See application file for complete search history.

(56) References Cited

U.S. PATENT DOCUMENTS

| | | | |
|---|---|---|---|
| 5,855,907 A | | 1/1999 | Peyman |
| 6,214,370 B1 * | | 4/2001 | Nelson et al. ................. 424/425 |
| 6,319,492 B1 * | | 11/2001 | Kohn et al. ................. 424/78.08 |
| 6,491,940 B1 * | | 12/2002 | Levin ............................ 424/434 |
| 2004/0018226 A1 * | | 1/2004 | Wnek et al. .................. 424/443 |
| 2005/0245906 A1 | | 11/2005 | Makower et al. |
| 2007/0083245 A1 * | | 4/2007 | Lamensdorf et al. ........... 607/45 |

* cited by examiner

*Primary Examiner* — Suzanne Ziska
(74) *Attorney, Agent, or Firm* — Roach Brown McCarthy & Gruber, P.C.; Kevin D. McCarthy

(57) ABSTRACT

A retrievable, sustained release, solid dosage form is provided for implanting into cranial bony canals and for prolonged release of an anesthetic, whereby treating neurovascular conditions, such as migraine. The dosage comprises an anesthetic contained in a polymeric carrier, and a retrieval member, the anesthetic being gradually released from the carrier.

13 Claims, 5 Drawing Sheets

SOLID DOSAGE FORM FOR TREATING HEADACHES

REFERENCE TO CO-PENDING APPLICATIONS

Priority is claimed as a 371 of international of PCT/IL2009/000314, filed on Mar. 19, 2009, which claims priority to U.S. provisional patent application Ser. No. 61/038,431 filed on Mar. 21, 2008.

FIELD OF THE INVENTION

The present invention relates to an implantable and retrievable polymer dosage loaded with anesthetic moiety for alleviating cerebral neurovascular conditions, particularly headache.

BACKGROUND OF THE INVENTION

The spenopalatine ganglion (SPG) is involved in many intracranial processes, including vasodilatation, vasoconstriction, inflammation, and pain. Sphenopalatine ganglion (SPG) blockade is reported to be effective in some patients suffering from migraine or cluster headaches. The first reference to such techniques originates in 1917 (see, for example, Ref. 1). Various surgical procedures are now available, the most popular of which is percutaneous SPG radiofrequency rhizotomy, reported to relieve pain after surgery. In addition, gamma knife radiosurgery of the trigeminal nerve and endoscopic ganglion blockade are also being used for the same purpose. Though the control of an acute pain attack may be achieved with local application of anesthetic agents, repetitive SPG blockade has not generally achieved acceptance in neurological circles. Pharmacological blockade of the SPG is based on transnasal, transoral, transpalatine, and lateral approaches of administration of nerve blocking agents such as lidocaine (Refs. 1-3). For example, the transnasal application of topical anesthetic is a simple and common technique (Ref. 7); however, the diffusion of topical anesthetic to the ganglion is difficult to control, and such a blockade is not durable. Topical anesthesia to the nasal mucosa between the middle and inferior turbinates from nares to the nasopharynx, followed by a needle insertion in the same tract, brought a longer relief.

Thus, nasal administration of local anesthetic and pharmacological agents such as lidocaine or cocaine was found to be effective both in relieving acute pain and for the long term control of pain, but it is extremely complicated to control dosage during nasal delivery of these agents, while clinical response being unpredictable. Furthermore, some nasal preparations have significant adverse effects, some are not well absorbed and therefore do not work consistently, and others are challenging due to their complex delivery ways.

Headache is a very common symptom, causing immense suffering to the patients, and it is often associated with disability; migraines afflict 24 million people in the US alone (Ref. 6). Managing the problem is complex and often unsuccessful. About one third of the migraine patients do not respond to the available treatments today or cannot stand the side effects. Many of those who can accept the available treatments are handicapped by the side effects such as confusion and drowsiness. Eventual use of local aesthetics might be helpful, but due to the mentioned drawbacks of the available delivery means, a need for improved delivery system is urgently felt. It is therefore an object of the invention to provide an efficient system for long term delivery of therapeutic agents, so addressing said current technological and clinical unmet needs.

It was demonstrated that an efficient nerve block anesthesia can be achieved via the greater palatine canal, enabling dental and oral surgery without general anesthetic (Refs. 3-5). It is therefore another object of the invention to provide an efficient method for long term delivery of therapeutic agents, comprising releasing said agents via a palatine canal and especially via the greater palatine canal.

It is a still another object of the invention to provide a method for treating a cerebral neurovascular disorder, comprising placing near the spenopalatine ganglion (SPG) a solid dosage ensuring a long-acting release of a pharmaceutical ingredient capable of partially or fully block the SPG.

It is further an object of the invention to provide a solid dosage ensuring a long-acting release of a pharmaceutical ingredient near a dorsonal nerve structure, such as SPG.

It is a still further object of the invention to provide a solid dosage ensuring a long-acting release of a pharmaceutical ingredient capable of reducing the severity and incidence of cranial pain.

It is also a further object of the invention to provide a solid dosage for use in alleviating or healing headache, such as migraine, cluster headache, and tension headache.

Other objects and advantages of present invention will appear as description proceeds.

SUMMARY OF THE INVENTION

This invention provides a retrievable solid, long-acting dosage form for implantation in elongated bony canals, such as palatine canal, comprising: i) a carrier member comprising a pharmaceutically acceptable polymer, the carrier member comprising an elongate structural support and optionally a film forming the external surface of said carrier member, the support comprising a distal end and a proximal end; ii) a local anesthetic contained in said carrier member; and a retrieval member located near said proximal end, and connected to said carrier member; wherein less than about 90% of the initial amount of said local anesthetic is released from said carrier member within a period of 30 days under nominal physiologic conditions. Said carrier member may comprise a biodegradable polymer, for example selected from the group consisting of starch, gelatin, dextran, dextrin, alginate, hydroxypropyl methylcellulose, hydroxypropyl cellulose, polyvinyl alcohol, poly (L-lactic acid), poly(lactide-co-glycolide), polyethylene glycol, polycaprolactone, polyphosphate ester, poly(hydroxy-butyrate), poly(glycolic acid), poly (DL-lactic acid), poly(amino acid), chitosan, collagen and cellulose, polyethylenecarbo-nate, and mixtures thereof. Said carrier may comprise a biostable polymer, selected for example from the group consisting of polycarbonate based aliphatic polyurethanes, siloxane based aromatic polyurethanes, polydimethyl-siloxane and other silicone rubbers, polyesters, polyolefins, polymethyl-methacrylate, vinyl halide polymers and copolymers, polyvinyl aromatics, polyvinyl esters, polyamides, polyimides, and polyethers. Said anesthetic may be selected from the group consisting of lidocaine, lidocaine salicylate monohydrate, cocaine, procaine, and 2-chloroprocaine, ambucaine, amylocaine, betoxycaine, bupivacaine, levo-bupivacaine, butacaine, butanilicicaine, butoxycaine, carticaine, cyclomethycaine, dibucaine, dimethocaine, levo-etidocaine, etidocaine, dextro-etidocaine, beta.-eucaine, fomocaine, hexylcaine, hydroxyprocaine, hydroxytetracaine, leucinocaine mesylate, levo-mepivacaine, mepivacaine, meprylcaine, metabutoxycaine, myrtecaine, octacaine, orthocaine, parethoxycaine, phenacaine, piperocaine, piridocaine, prilocaine, propanocaine, proparacaine, propipocaine, propoxycaine, pseudococaine, pyrrocaine, risocaine, ropivacaine, levo-ropivacaine, tetracaine, tolycaine, trimecaine, and pharmaceutically acceptable salts thereof. In a preferred embodiment of the invention, said elongate structural support is adapted to preferentially allow diffusion of said local anesthetic near said distal end. Said retrieval member is preferably adapted to allow dislocation of said dosage form in one piece, in the distal to proximal direction, at any time period following its implantation. In a preferred embodiment, said carrier member comprises a fiber matrix which comprises anesthetic. Said elongate structural support may have a length of from about 5 to 15 mm, and it may have a cross section of from about 0.2 mm$^2$ to about 2 mm$^2$. Said elongate structural support may comprises a core skeleton, said skeleton comprising one or more longitudinal axes and plurality of lateral projections emanating therefrom, wherein said lateral projections may be distributed between said distal end to said proximal end thereof and may be preferably adapted to facilitate the spatial integration of said support and said film in said carrier member. Said carrier member or its part may be electrospun from solution jointly with said anesthetic. Said carrier member may comprise a fibrous matrix with said anesthetic bound on and in the polymer fibers. Said film forms an external surface of said elongate structural support, whereas said carrier member and said anesthetic are substantially contained within a volume defined by said distal end, said proximal end, and said external surface. Said film comprises a pharmaceutically acceptable polymer. The film may comprises PTFE. In one embodiment, diffusion of said anesthetic through said film near said distal end is at least 10 times greater than near said proximal end. Said external surface is preferably adapted to minimize the attachment thereto of fibrous tissues growing in its environment after placing the dosage form in the bony canal.

The invention is directed to a method of inhibiting a cerebral neurovascular disorder in a patient, the method comprising placing into a palatine canal adjacent to a dorsonasal nerve structure of said patient a solid dosage form as described above, thereby anesthetizing said dorsonasal nerve structure and inhibiting said cerebral neurovascular disorder for a period greater than one month. Said cerebral neurovascular disorder may be selected from the group consisting of tinnitus, seizure, ischemic event, and headache. Said headache may be selected from the group consisting of migraine, cluster headache, and tension headache. The method of the invention is particularly useful for treating an acute migraine episode. Said palatine canal is preferably the greater palatine canal. Said dorsonasal nerve structure preferably comprises sphenopalatine ganglion (SPG). In a preferred method according to the invention, said solid dosage form is placed into pterygopalatine fossa of the patient, thereby inhibiting said disorder for a period greater than one month; said inhibiting the disorder may comprise either healing the disorder or alleviating a symptom, and it may comprise preventing the symptoms—preferably preventing fully developed migraine. Said placing a solid dosage form into a palatine canal may comprise injecting, or other known minimally invasive introduction techniques.

The invention provides a retrievable, long-acting solid dosage form for use in inserting via a bone canal, particularly a palatine canal, and preferably the greater palatine canal, and inhibiting a cerebral neurovascular disorder in a patient for a period greater than one month, the dosage form comprising i) a carrier member comprising an elongate structural support and optionally a film forming the external surface of said carrier member, the support comprising a distal end and a proximal end; ii) a local anesthetic contained in said carrier member; and a retrieval member located near said proximal end and connected to said carrier member; wherein less than about 90% of the initial amount of said local anesthetic is released from said carrier member within a period of 30 days under nominal physiologic conditions. Said disorder may be selected from the group consisting of tinnitus, seizure, ischemic event, and headache. Said headache may be selected from the group consisting of migraine, cluster headache, and tension headache. Said headache particularly comprises an acute migraine episode.

BRIEF DESCRIPTION OF THE DRAWINGS

The above and other characteristics and advantages of the invention will be more readily apparent through the following example, and with reference to the appended drawings, wherein.

DETAILED DESCRIPTION OF THE INVENTION

Figure 1:
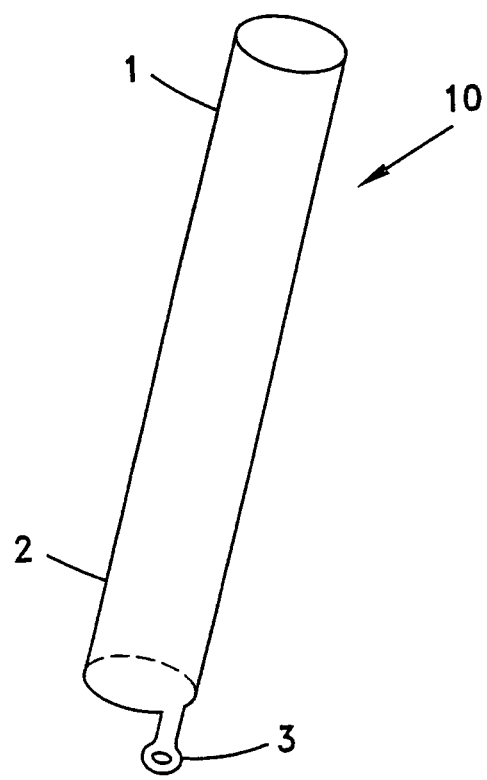
FIG. 1. schematically depicts an embodiment of the retrievable solid dosage of the invention (10), for implanting in a cranial canal, such as in greater palatine canal; a cylindrical carrier member is shown provided with a retrieval member (3); the positions of a distal end (1) and a proximal end (2) of a structural support behind the external surface are outlined; the cylinder dimensions are usually about 5-15 mm in length and 0.5-1.5 mm in diameter.
Figure 2:
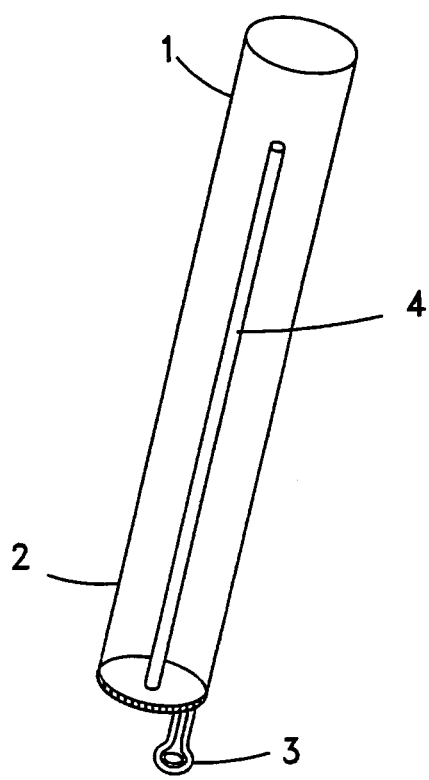
FIG. 2. schematically depicts an embodiment of the retrievable solid dosage of the invention; a cylindrical carrier member provided with a retrieval member (3) is shown; the positions of a distal end (1) and a proximal end (2) are outlined; a structural support (4) is schematically depicted behind the external surface.
Figure 3:
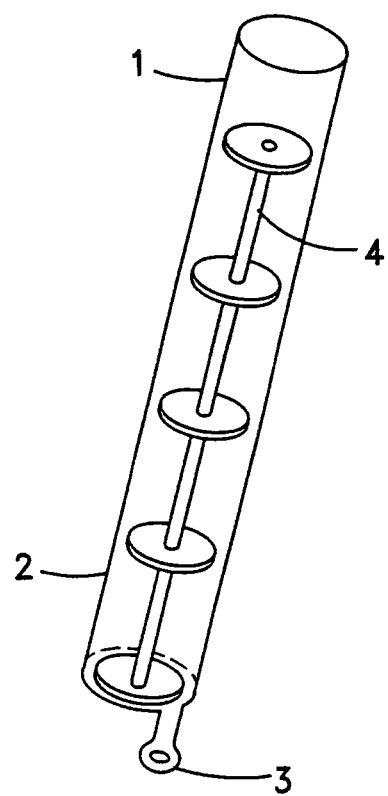
FIG. 3. schematically depicts an embodiment of the retrievable solid dosage of the invention; an approximately cylindrical carrier provided with a retrieval member (3) is shown; further a core skeleton of the structural support (4) comprising one longitudinal axe and five lateral projections is schematically depicted behind the external surface film; said support together with an anesthetic are substantially contained within a volume defined by said distal end, said proximal end, and said cylinder surface.
Figure 4:
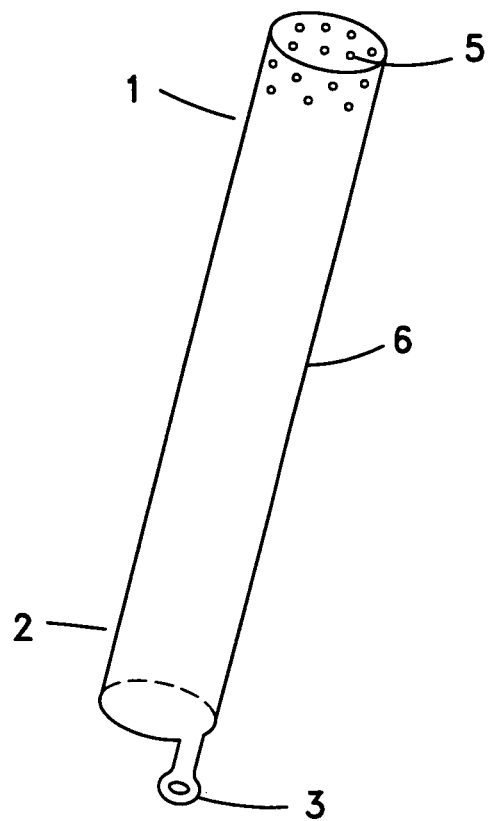
FIG. 4. schematically depicts an embodiment of the retrievable solid dosage of the invention; a cylindrical carrier member provided with a retrieval member (3) is shown; the positions of a distal end (1) and a proximal end (2) are outlined; the external surface made of polymeric film is depicted (6); a region of facilitated diffusion for said anesthetic is shown (5) near said distal end, possibly realized by a plurality of perforations in the film.
Figure 5:
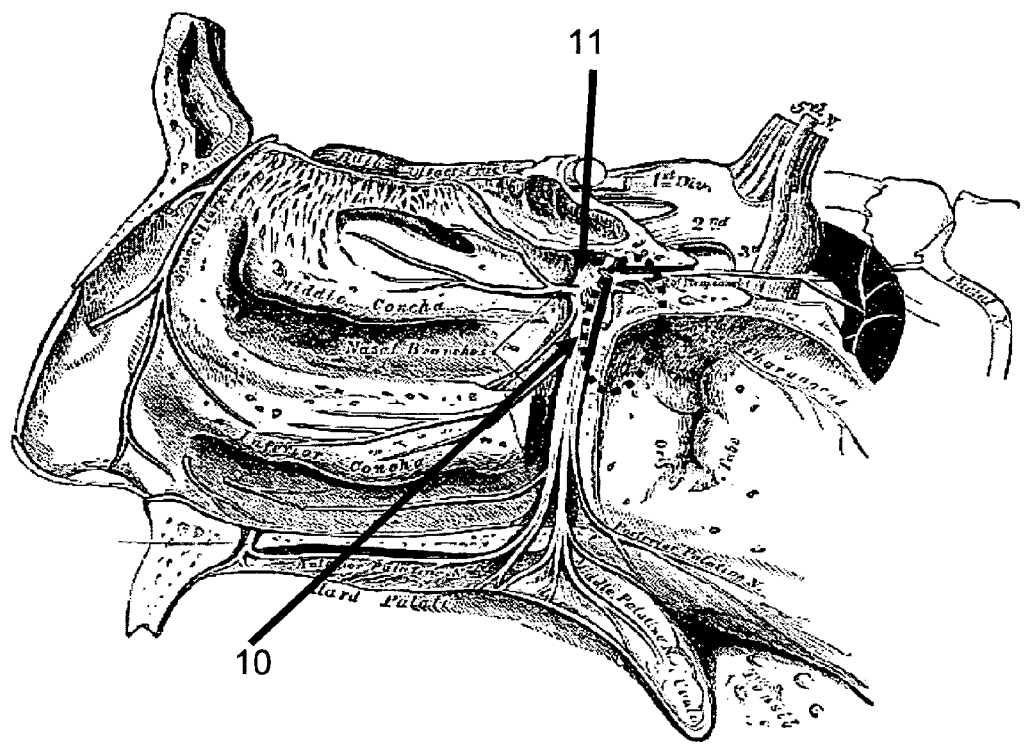
FIG. 5. schematically depicts a para-saggital cross-section of a human head, showing the location of the sphenopalatine ganglion (11) and a postero-laterally-positioned retrievable solid dosage form (10) circled by a dotted line.

A retrievable solid dosage shaped to be inserted into elongated cranial bony canals has now been provided for treating headache and other cerebral neurovascular disorders. A surprisingly effective design comprises a thin elongated carrier shaped for inserting to a bony canal, such as the greater palatine canal, and a slowly released anesthetic which locally affects adjacent dorsonasal nerve structure, wherein the effects may be continued for months and more, or they may be discontinued by removing said dosage—according to the medical situation.

Provided is a system for inhibiting a cerebral neurovascular disorder in a human patient, comprising a retrievable solid dosage form to be placed into a palatine canal adjacent a dorsonasal nerve structure of a patient, wherein said solid dosage form comprises (i) a pharmaceutically acceptable polymer, (ii) a long-acting pharmaceutical, (iii) an elongate structural support member, and (iv) a retrieval member, said solid dosage form being capable of anesthetizing said dorsonasal nerve structure so as to inhibit said cerebral neurovascular disorder for a period greater than one month, possibly for a period of between about three to six months. Of course, in cases where a complication may occur, or in cases where severe adverse side effects are manifested—the dosage form may be easily retrieved. Said pharmaceutical is preferably an anesthetic. Nonetheless, there are other active pharmaceutical entities that may have the capability to reduce conduction in nerves and would therefore also be useful in the solid dosage of the invention. In an important aspect of the invention, the purpose of the dosage form is to reduce the firing rate of the SPG, and this may be achieved with various pharmaceuticals, including anesthetics.

Said cerebral disorder may comprise an ischemic event, tinnitus, cerebrovascular spasm, or a seizure. Involved may be condition manifested during or after an acute ischemic event. In a preferred embodiment of the invention, the system for inhibiting a cerebral disorder, as well as the retrievable dosage and the method of using it, is employed in treating a headache. The treatment may comprise healing headache or alleviating the symptoms; in other aspect of the invention, the treatment may comprise preventing headache by locating the retrievable dosage in said cranial canal on appearance of prodromal symptoms. The treatment will preferably inhibit the symptoms, or it will decrease the frequency or severity of attacks. The headache may comprise a migraine, a cluster headache, or a headache associated with a vascular disease. Conditions to be treated by the present system may comprise acute cerebral neurovascular disorder, possibly comprising a tinnitus episode, an individual seizure, an episode of cerebrovascular spasm, an acute migraine episode, an individual headache episode associated with a cluster headache, and an individual headache associated with a vascular disease. The system will be particularly appreciated during an acute migraine episode. Particularly, said canal is the greater palatine canal, and said dorsonasal nerve structure is the sphenopalatine ganglion (SPG). The dorsonasal nerve structure affected by the present system is SPG or a neural structure directly connected with it. The term cerebral neurovascular disorder is used herein for a pathological condition associated with cerebral vascular or cerebral nervous system. The term dorsonasal nerve structure includes SPG and nerve structures near to it.

In one aspect, the invention provides a method of inhibiting a cerebral neurovascular disorder in a human patient, the method comprising placing into a pterygopalatine fossa, or near to it, adjacent a dorsonasal nerve structure of a patient a solid dosage form comprising (i) a pharmaceutically acceptable polymer, and (ii) a long-acting local anesthetic, and (iii) an elongate structural support member, and (iv) a retrieval member; whereby said solid dosage form is capable of anesthetizing said dorsonasal nerve structure so as to inhibit said cerebral neurovascular disorder for a period greater than one month. Said disorder is selected from the group consisting of tinnitus, cerebrovascular spasm, seizure, a neurovascular headache, and conditions manifested during or after an acute ischemic event. In a preferred embodiment, the method according to the invention enables treating a migraine. An acute cerebral neurovascular disorder may be treated, selected from the group consisting of a tinnitus episode, an individual seizure, an episode of cerebrovascular spasm, an acute migraine episode, an individual headache episode associated with a cluster headache, and an individual headache associated with a vascular disease. The method of the invention may be employed following the onset of a prodromal symptom of a cerebral neurovascular disorder in the patient.

Said dorsonasal nerve structure is preferably sphenopalatine ganglion. Said dorsonasal nerve structure may be a neural structure directly connected with sphenopalatine ganglion of said patient. The dosage form of the invention is anatomically shaped or may assume such a shape, so as to be insertable via a bony canal; in particular—cranial bony canal; more specifically—the palatine bony canal. It is to be noted that in the context of the present invention, the term palatine canal refers, if not stated otherwise, either to the greater palatine canal, or to the lesser palatine canal, or to their superior extention, also known as pterygopalatine (or sphenopalatine) fossa.

Said pharmaceutical, used in the system according to the invention, may be selected from lidocaine, lidocaine salicylate monohydrate, cocaine, procaine, 2-chloroprocaine, ambucaine, amolanone, amylocaine, benoxinate, betoxycaine, biphenamine, bupivacaine, levo-bupivacaine, butacaine, butamben, butanilicicaine, butethamine, butoxycaine, carticaine, cocaethylene, cyclomethycaine, dibucaine, dimethisoquin, dimethocaine, diperodon, dyclonine, ecgonidine, ecgonine, ethyl aminobenzoate, levo-etidocaine, etidocaine, dextro-etidocaine, beta-eucaine, euprocin, fenalcomine, fomocaine, hexylcaine, hydroxyprocaine, hydroxytetracaine, isobutyl p-aminobenzoate, leucinocaine mesylate, levoxadrol, meperidine, levo-mepivacaine, mepivacaine, meprylcaine, metabutoxycaine, myrtecaine, naepaine, octacaine, orthocaine, oxethazaine, parethoxycaine, phenacaine, pipecoloxylidide, piperocaine, piridocaine, polidocanol, pramoxine, sameridine, prilocaine, propanocaine, proparacaine, propipocaine, propoxycaine, pseudococaine, pyrrocaine, quinine urea, risocaine, ropivacaine, levo-ropivacaine, salicyl alcohol, tetracaine, tolycaine, trimecaine, veratridine, zolamine, adenosine, adenosine monophosphate, adenosine diphosphate, adenosine triphosphate, and pharmaceutically acceptable salts thereof, or other pharmaceuticals having an inhibitory effect on nerve signal conduction.

In one embodiment, the solid dosage form according to the invention may be provided with a retrieval member which allows dislocation of said dosage form in one piece in the distal to proximal direction, following its implantation at any time period in the range between about 1 to 365 days under normal physiologic conditions.

In other embodiment, the solid dosage form may comprise steroids, phenol or other pharmacologic agents to the SPG for treatment of trigeminal neuralgia, migraine, cluster headaches, or atypical facial pain. The dosage comprises a pharmacological agent formulated into a biodegradable matrix rod implanted into the SPG canal, releasing pharmacological moiety locally for a long term duration in a controlled manner.

In one embodiment of the invention, a solid dosage form is provided comprising a pharmaceutically acceptable polymer, possibly having a morphology of a fiber matrix. The involved fibers may have a diameter in the range between about 50 nm and 5000 nm. A locally acting anesthetic is associated with the fiber matrix. In one embodiment, the fibers are impregnated with the anesthetic. The polymer which forms the carrier member or the structural support, may be soaked in an anesthetic solution or suspension, and dried. The polymer and anesthetic may be jointly electrospun from solution. Any method known in the art may be employed for preparing a stable form of the carrier member loaded with the anesthetic. An polymer envelope having a diameter in the range between 50 nm and 5000 nm surrounds the carrier member and limits the diffusion of said pharmaceutical out of the matrix.

The length of the dosage form is preferably in the range between 5 mm and 15 mm and its two other dimensions are in the range between 0.5 mm and 1.5 mm. The carrier member may, for example, have a shape close to a cylinder 5-15 mm long with a diameter of 0.5-1.5 mm, essentially filled with fibrous matrix impregnated with an anesthetic and surrounded by a 50-5000 nm membrane determining the diffusion rate of the anesthetic into the bone canal, while the matrix is formed by entangled fibers. The dosage may comprise, for example, 0.5-5 mg lidocaine.

In one possible embodiment of the present invention, the dosage form would have the morphology of a fiber matrix. In this case, the anesthetic or other pharmaceutical may be dissolved in the polymer fibers, or it may be entrapped in the form of micro or nano particles between the polymer fibers or within the fibers themselves. In one embodiment of the invention, the solid dosage is prepared by mixing a pharmaceutical, such as lidocaine, with a carrier polymer, such as PLGA, while dissolving both in an organic solvent, such as DMSO. Subsequently, the dissolved polymer and pharmaceutical are poured into a mold already containing the structural support which provides mechanical integrity to the dosage form.

In one embodiment, the carrier polymer is biodegradable, and both the structural support and the retrieval member are biostable. A polymeric film, eventually added to the dosage form to cover its external surface, further i) reduces friction when injecting or inserting the dosage form, or when trying to retrieve it, enables to affect the pharmaceutical release, for example by reducing the overall diffusion rate or by selectively changing the diffusion rate near said distal end, and may increase the integrity of the dosage, which also helps in retrieving the dosage form. A polymeric film, such as ePTFE, will further reduce the level of connective tissue growth into the dosage form.

The terms proximal and distal in this text relate to the dosage orientation; physician that is implanting the dosage form will know that the distal part goes into the bony canal first and is located adjacent the SPG, while the proximal end is closer to the (hard) palate of the oral cavity.

The invention is thus directed to dosage forms and methods for treating cerebral neurovascular conditions, particularly headaches, utilizing local aesthetics but overcoming drawbacks of the available therapeutic means. Provided is an efficient system for long term delivery of therapeutic agents, so addressing current technological and clinical unmet needs. In one aspect, provided is an efficient method for long term delivery of therapeutic agents, comprising releasing said agents into the greater palatine canal. In other aspect of the invention, provided is a method for treating a cerebral neurovascular disorder, comprising placing near the SPG a solid dosage ensuring a long-acting release of local anesthetic. The method is particularly useful in treating cranial pain. The invention also provides a solid dosage for use in mitigating or healing headache, such as migraine, cluster headache, and tension headache.

The invention will be further described and illustrated by the following example.

EXAMPLES

Lidocaine hydrochloride powder was mixed with RESOMER® RG 858 S [poly(D,L-lactide-co-glycolide, PLGA] purchased from Bohringer Ingelheim (CAS number 26780-50-7, material number 63292) in a 1:1 weight ratio; both were dissolved in DMSO and placed on a flat bed for the DMSO to fully evaporate. Thereafter, the preparation was put in a mild vacuum chamber for further removal of DMSO residues. Subsequently, rectangles of lidocaine HCl/PLGA solid dosage forms were cut to shape.

While the invention has been described using some specific examples, many modifications and variations are possible. It is therefore understood that the invention is not intended to be limited in any way, other than by the scope of the appended claims.

REFERENCES

1. Maxillary Nerve Block: The Pterygopalitine Canal Approach; Hawkins J. M. and Isen D.; Copyright 1998 *Journal of the California Dental Association*, URL: www.cda.org/library/cda_member/pubs/journal/jour998/maxilla.html;
2. Laser-Doppler Blood Flowmetry Measurement of Nasal Mucosa Blood Flow after Injection of the Greater Palatine Canal; Gurr P, Callanan V, and Baldwin D.; J. Laryngol. Otol. 110(2), 1996, 124-8;
3. Maxillary Nerve Block: A New Approach Using a Computer-Controlled Anesthetic Delivery System for Maxillary Sinus Elevation Procedure, a Prospective Study; Schwartz-Arad D, Dolev E, Williams W.; Quintessence Int. 35(6), 2004, 477-80;
4. Maxilliary Nerve Block Anaesthesia via the Greater Palatine Canal: A Modified Technique and Case Reports; Wong J. D. and Sved A. M.; Aust. Dent. J. 36(1), 1991, 15-21;
5. Maxilliary Nerve Block via the Greater Palatine Canal: New Look at an Old Technique; Lepere A. J.; Anesth. Pain Control Dent. 2(4), 1993, 195-7;
6. The Merck Manual of Diagnosis and Therapy, $17^{th}$ Ed., Merck & Co. Inc. 1999.
7. U.S. Pat. No. 5,855,907, Peyman, 1999

The invention claimed is:

1. A retrievable solid, long-acting dosage form for implantation in a palatine canal of a patient for releasing a local anesthetic near sphenopalatine ganglion (SPG) for a period of between 1 and 6 months, whereby anesthetizing a dorsonasal nerve structure and inhibiting a cerebral neurovascular disorder in the patient, comprising:
   i) a carrier member comprising an elongate structural support having a length of from about 5 mm to 15 mm, and a pharmaceutically acceptable polymer film having a width of between 50 and 5000 nm and comprising a plurality of perforations, forming the external surface of said carrier member through which said anesthetic diffuses to said canal of the patient, the support comprising a distal end and a proximal end;
   ii) a local anesthetic mixed with PLGA contained in said carrier member; and
   iii) a retrieval member located near said proximal end, and connected to said carrier member;
   wherein the diffusion of said anesthetic through said film near said distal end is at least 10 times greater than near said proximal end.

2. A solid dosage form according to claim 1, wherein said anesthetic is selected from the group consisting of lidocaine, lidocaine salicylate monohydrate, cocaine, procaine, and 2-chloroprocaine, ambucaine, amylocaine, betoxycaine, bupivacaine, levo-bupivacaine, butacaine, butanilicicaine, butoxycaine, carticaine, cyclomethycaine, dibucaine, dimethocaine, levo-etidocaine, etidocaine, dextro-etidocaine, beta.-eucaine, fomocaine, hexylcaine, hydroxyprocaine, hydroxytetracaine, leucinocaine mesylate, levo-mepivacaine, mepivacaine, meprylcaine, metabutoxycaine, myrtecaine, octacaine, orthocaine, parethoxycaine, phenacaine, piperocaine, piridocaine, prilocaine, propanocaine, proparacaine, propipocaine, propoxycaine, pseudococaine, pyrrocaine, risocaine, ropivacaine, levo-ropivacaine, tetracaine, tolycaine, trimecaine, and pharmaceutically acceptable salts thereof.

3. A solid dosage form according to claim 1, wherein said elongate structural support is adapted to preferentially allow diffusion of said local anesthetic near said distal end.

4. A solid dosage form according to claim 1, wherein said retrieval member is adapted to allow dislocation of said dosage form in one piece, in the distal to proximal direction, at any time period following its implantation.

5. A solid dosage form according to claim 1, wherein said carrier member comprises a fiber polymeric matrix, which matrix comprises said anesthetic.

6. A solid dosage form according to claim 1, wherein said elongate structural support has a cross section of from about 0.2 mm$^2$ to 2 mm$^2$.

7. A solid dosage form according to claim 1, wherein said elongate structural support comprises a core skeleton, said skeleton comprising one or more longitudinal axes and plurality of lateral projections emanating therefrom, and wherein said lateral projections being distributed between said distal end to said proximal end thereof and being adapted to facilitate the spatial integration of said support and said film in said carrier member.

8. A solid dosage form according to claim 1, wherein said carrier member or its part and said anesthetic are jointly electrospun from solution.

9. A solid dosage form according to claim 1, wherein said film forms an external surface of said elongate structural support, and wherein said carrier member and said anesthetic are substantially contained within a volume defined by said distal end, said proximal end, and said external surface.

10. A solid dosage form according to claim 1, wherein said external surface is adapted to minimize the attachment of fibrous body tissues thereto.

11. A method of inhibiting a cerebral neurovascular disorder in a patient, the method comprising placing into a palatine canal adjacent to a dorsonasal nerve structure of said patient a solid dosage form according to claim 1, thereby anesthetizing said dorsonasal nerve structure and inhibiting said cerebral neurovascular disorder for a period greater than one month, said cerebral neurovascular disorder being selected from the group consisting of tinnitus, seizure, ischemic event, and headache selected from the group consisting of migraine, cluster headache, and tension headache.

12. A method according to claim 11, wherein said inhibiting the disorder comprises healing, alleviating, or preventing migraine.

13. The method according to claim 11, wherein said placing comprises injecting.

* * * * *